United States Patent [19]

Olson

[11] Patent Number: 4,535,774

[45] Date of Patent: Aug. 20, 1985

[54] STROKE VOLUME CONTROLLED PACER

[75] Inventor: Walter H. Olson, North Oaks, Minn.

[73] Assignee: Medtronic, Inc., Minneapolis, Minn.

[21] Appl. No.: 509,573

[22] Filed: Jun. 30, 1983

[51] Int. Cl.³ .............................................. A61N 1/36
[52] U.S. Cl. ............................................ 128/419 PG
[58] Field of Search .............. 128/419 P, 419 PG, 713

[56] References Cited

U.S. PATENT DOCUMENTS

| 4,303,075 | 12/1981 | Heilman et al. | 128/419 PG |
| 4,399,820 | 8/1983 | Wirtzfeld et al. | 128/419 PG |
| 4,436,092 | 3/1984 | Cook et al. | 128/419 PG |

Primary Examiner—William E. Kamm
Assistant Examiner—Mitchell J. Shein
Attorney, Agent, or Firm—Robert C. Beck; John L. Rooney; Joseph F. Breimayer

[57] ABSTRACT

A rate responsive pacer which paces the heart at a rate dependent on detected variations in the stroke volume of the heart.

6 Claims, 3 Drawing Figures

A. NORMAL HEART

B. PACED HEART

C. PACING WITH FIXED STROKE VOLUME SET POINT

D. PACING WITH FLOATING STROKE VOLUME SET POINT

STROKE VOLUME CONTROLLED PACER

BACKGROUND OF THE INVENTION

This invention relates generally to the field of cardiac pacemakers, and more particularly, to a pacemaker having an escape interval which is set in response to a measured physiologic variable of the patient.

When the body undergoes exercise, a variety of changes take place. These include an increase in respiration, diversion of blood flow to the active skeletal muscles, and an increase in cardiac output. These changes cooperate to deliver an increased amount of oxygen and nutrients to the active muscles.

The mass flow rate of oxygenated blood from the heart is referred to as the cardiac output of the heart, and it is equal to the product of the heart rate in beats per minute and the heart's stroke volume in liters.

The increase in cardiac output is achieved by an increase in the stroke volume of the heart; up to two fold, as well as an increase in the heart rate; up to three fold.

The changes in stroke volume are mediated by venous return, contractility and afterload, while the changes in the heart's rate are mediated through the autonomic nervous system which operates on a structure called the S-A Node.

The S-A Node is located on the atria of the heart. An electrical signal generated by this natural pacemaker causes the atria, or upper chambers of the heart to contract. This forces blood into the lower chambers or ventricles of the heart. The signal from the S-A Node is propagated to the lower chambers of the heart through a structure called the Atrio-Ventricular or A-V Node after a brief delay. The signal from the A-V Node causes the ventricles to contract, forcing the blood throughout the body.

Many forms of heart disease impare the function of the S-A and A-V Nodes, and their associated conductive tissues. Patients exhibiting these indications may be candidates for artificial pacemaker therapy.

Initially, pacemakers were implanted in patients who exhibited complete A-V block. This conduction disturbance is manifested by the inability of the signal from the S-A Node to reach the lower chambers of the heart to initiate a ventricular contraction.

The earliest form of implantable pacemaker for the long-term stimulation of the heart is known from U.S. Pat. No. 3,057,356 issued to W. Greatbatch. This asynchronous pacemaker, in essence, replaced the heart's natural conduction system and periodically provided an electrical stimulus to the ventricle to cause contractions.

In some patients, the A-V block condition is intermittant and occasionally the artificial pacemaker and the natural S-A Node of the heart complete for control of the ventricular action of the heart. This competition is undesirable. The demand pacemaker avoids this competitive pacing. An example of an implantable version of the demand pacemaker is known from U.S. Pat. No. 3,478,746, to W. Greatbatch.

In operation, the demand mode pacemaker senses the ventricular contraction of the heart, and provides stimulation to the ventricles only in the absence of a naturally occurring contractions of the heart. Such demand pacemakers synchronize their timing with the heart and provide stimulated beats if the natural cardiac rhythm drops below a preset rate. Both the asynchronous and demand type of pacemaker thus provided for a fixed lower rate for the patient's heart rate.

When a patient has no intrinsic rhythm and is being paced at a fixed rate, any increment in demand for cardiac output must come solely from naturally induced changes in stroke volume. For these patients, strenous work is impossible since stroke volume changes alone are insufficient to raise the cardiac output enough to supply the skeletal muscles during heavy exercise.

By way of contrast, the P-synchronous mode of pacemaker, as exemplified by U.S. Pat. No. 3,253,596 to J. W. Keller, monitored electrical activity in the atrium, and triggered a ventricular action after a short time period. This form of pacemaker permits the patient's naturally occurring atrial rate to control the rate of ventricular stimulation.

Other pacemakers which exhibit the atrial tracking feature include the atrial-synchronized, ventricularly inhibited pacemaker known from U.S. Pat. No. 3,648,707 to W. Greatbatch, as well as the dual-sense, dual-pace pacemaker known from U.S. Pat. No. 4,312,355 to H. Funke. The advantage of atrial synchronized pacing is that it permits the pacemaker's rate to be determined by the S-A Node which in turn intrepreats the body's demand for cardiac output.

Another form of rate adaptive pacer is known from U.S. Pat. No. 4,298,007 to Wright et al. This device monitors the artrial rate and alters the ventricular escape interval in response to the atrial rate.

For these patients, the pacemaker mimics the natural conductive system of the heart and increased demand for cardiac output comes from both an increase in heart rate controlled by the S-A Node as well as concomitant increase in stroke volume.

However, in many patients, the S-A Node is not a reliable source of information concerning the body's demand for cardiac output. Incorporating an S-A Node replacement to provide rate adaptive pacing would be desirable.

One form of rate responsive pacemaker which relies on the detection of blood saturation of oxygen is known from U.S. Pat. No. 4,202,339 to Wirtzfield. This device utilizes an optical measuring probe which is inserted into the heart to monitor the oxygen saturation of the blood. This measurement is then used to alter the stimulating frequency of an associated pacemaker.

Another form of rate responsive pacemaker is known from U.S. Pat. No. 4,009,721 to Alcidi. This device utilizes a pH measurement probe which alters the pacemaker's rate in response to the measurement of blood pH.

Another form of rate adaptive pacemaker is known from U.S. Pat. No. 4,140,132 to Dahl, which utilizes an accelerometer to monitor the physical activity of the patient, and which alters the pacemaker's escape interval.

Another form of rate adaptive pacer is known from U.S. Pat. No. 4,228,803 to Rickards. This patent discloses a pacer which monitors the Q-T interval of the cardiac cycle and increases the pacer rate in response to shortening of the Q-T interval.

Each of the preceding pacemakers has taken advantage of a physiologic parameter which varies with the body's demand for cardiac output.

Returning to cardiac physiology, and in reference to FIG. 3A it is important to note that the cardiac output of the heart, measured in liters of blood per minute, is the product of the patient's heart rate times the stroke volume of the heart. The figure shows a family of constant cardiac output curves called isopleths corresponding to cardaic outputs of 1 to 6 L/M. As previously indicated, increased physical activity in normal individuals, results in an increased cardiac output. In the normal heart, both the heart rate and the stroke volume increase to satisfy the body's need for oxygenated blood. Studies by Versteeg (1981) show that for exercise this cardiac transfer function is a first order linear function with a 10–12 second time constant. This normal cardiac response to increasing work loads is shown by the cardiac load line 300 on FIG. 3a. In the figure, a work load corresponding to cardiac output of 2 L/M is met by a heart rate of 75 bpm at a stroke volume of 26 ml. An increase in work load calling for a cardiac output of 5 L/M is met with a rate increase to 140 bpm and a stroke volume increase to 36 ml.

In those patients who have complete heart block and a fixed-rate pacemaker, it has been noted that increased demand for cardiac output due to physical exertion results in an increase in the measured stroke volume of a patient's heart. This is depicted in FIG. 3b, where the load line 310 corresponds to pacing at a fixed rate, as in asynchronous (VOO), demand pacing (VVI) or A-V sequential (DVI) pacing. This figure indicates that those paced patients who have S-A Node dysfunction can only change stroke volume in response to exercise. For example, at 2 L/M of cardiac output this patient exhibits a stroke volume of 20 ml at a rate of 100 bpm. An increase to 5 L/M calls for a stroke volume increase to 50 ml which may well be beyond the patient's capability.

Thus, the prior art discloses rate adaptive pacers which monitor a physiologic parameter.

Additionally, the response of the heart's stroke volume to physical exertion is well-known in the art.

BRIEF SUMMARY OF THE INVENTION

In contrast to thses preceding forms of rate variable pacemakers, the pacemaker of the present invention monitors the stroke volume of the patient and alters the pacing rate in accordance with an algorithm. The system controls the patient's heart rate and also permits the stroke volume of the patient's heart to vary over a controlled range.

DESCRIPTION OF THE PREFERRED EMBODIMENT

The present invention combines three pacer subsystems with the heart to form a closed loop pacer for pacing the heart.

Figure 1:
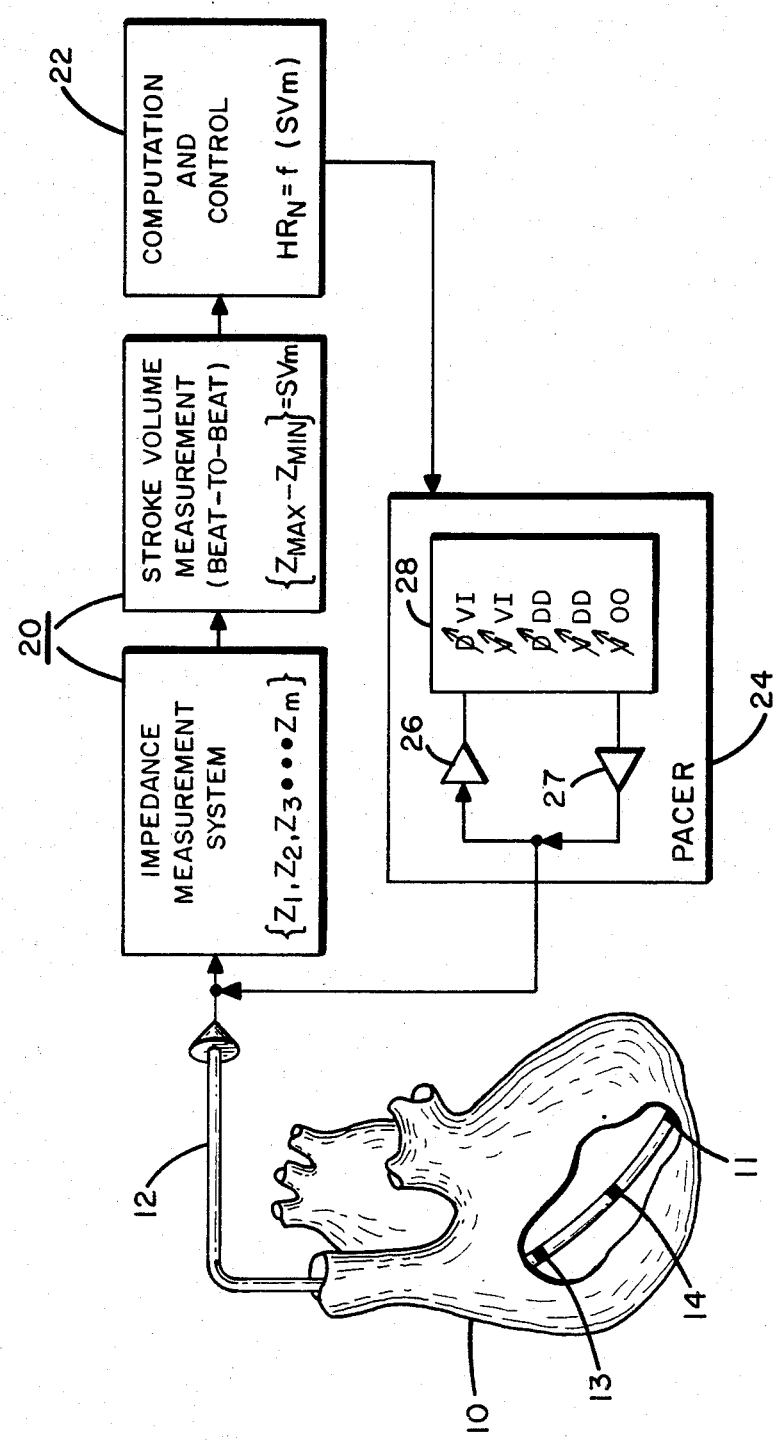
FIG. 1 is a block diagram of a pacemaker incorporating the invention.

In FIG. 1, the heart 10 is coupled to a stroke volume measurement apparatus 20 through a lead system 12. The stroke volume measurement system 20 delivers information regarding the stroke volume of the heart to computation and control logic 22. This apparatus utilizes information related to stroke volume to determine a desired pacing rate for the heart. Rate control information is provided to a pulse generator 24 which may provide stimulation to the heart 10 through lead system 12. The pulse generator 24 may operate in any of the known stimulation modes. However, the algorithm is described in the context of a rate variable asynchronous or VOO mode pacer. A system suitable for incorporating the output data of the algorithm into a demand mode pacer may be found in U.S. patent application Ser. No. 323,507 filed Nov. 23, 1981 and assigned to the Assignee of the present invention and is hereby incorporated by reference.

STROKE VOLUME MEASUREMENT SYSTEM

In response to an increase in demand for cardiac output the normal heart increases both its rate and stroke volume. The present invention utilizes the body's demand for cardiac output to control the rate of pacing. This technique requires a reliable measurement of a physiologic variable which is related to cardiac stroke volume.

Stroke volume may be inferred by a variety of measurements, taken in the right or left heart including pressure-time histories of arterial blood flow, as well as direct flow measurements in the major blood vessels of the heart.

Another method of determining the stroke volume of the heart is through the technique of impedance plethysmography. This technique has been widely studied (Rushmer 1953, Geddes 1966, Baan 1981). In this technique an electrode system is inserted into the right or left heart. As shown in FIG. 1 current is passed from an anode 13 to a cathode 14 and the voltage between the electrode pair is measured. The accuracy of this method may be increased by utilizing a multiplicity of electrode pairs. (Baan 1981). The magnitude of the voltage measurements from the sensing electrode pairs is a function of the impedance of the heart cavity, $(Z_m)$. This impedance is, in turn, a function of the volume of the chamber. In general, volume resistivity of the blood remains constant, and the magnitude of the voltage sensed depends solely upon the volume of the chamber during the measurement.

One may measure chamber volume sequentially ($Z_1$, $Z_2$, ... $Z_m$) over the entire cardiac cycle and can be used to ascertain the maxima and minima of cardiac chamber volume. However, in general, the maximum cardiac volume is achieved at end diastole just prior to the contraction of the ventricle. Likewise, the minimum volume of the ventricle occurs at the end of the contraction of the ventricular muscles called end systole. By measuring the heart volume at end systole and end diastole the stroke volume measurement apparatus may determine the stroke volume for that cardiac contraction or cycle. The computation and control circuitry which receives the stroke volume measurement information may average the stroke volume measurements over a number of cardiac cycles or may operate on a beat-to-beat basis. Further details regarding the measurement of stroke volume through the use of an intracardiac catheter may be found in *Cardiovascular Research*, 1981, 15, 328–334.

COMPUTATION AND CONTROL APPARATUS

Figure 2:
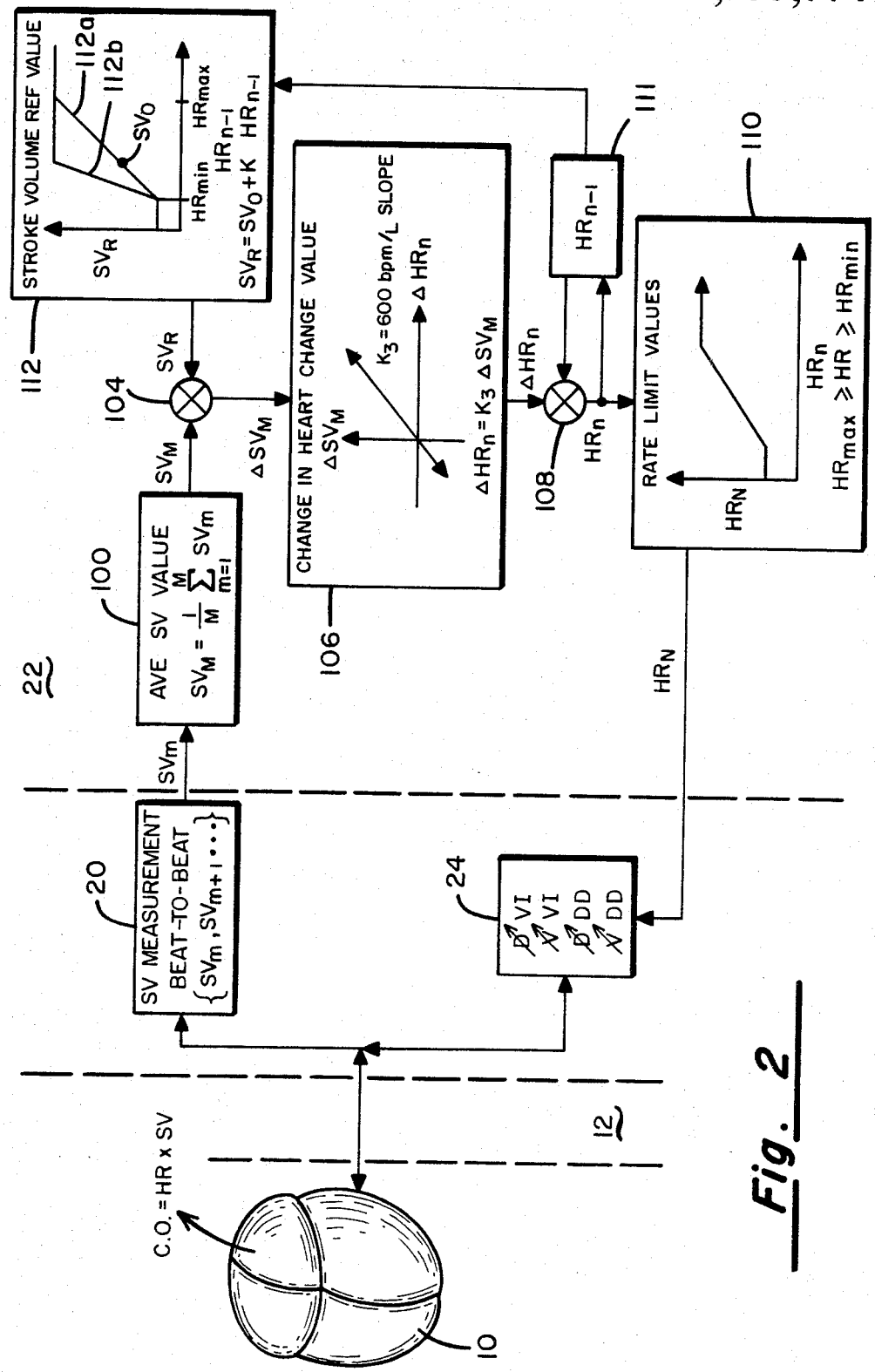
FIG. 2 is a flow chart and a functional block representation of the algorithm of the present invention.

The structural and functional aspects of computation and control system 22 are shown in FIG. 2.

The computation and control system 22 receives stroke volume information labeled SVm on a beat-to-beat basis from the stroke volume measurement system 20 which, in turn, is coupled to heart 10. The computation and control system 22 operates on this information and generates a heart rate value labeled $HR_N$. This rate information is used to control the escape interval of the pulse generator 24 portion of the pacer.

The system of sequential stroke volume measurements, denoted [$SVm$, $SVm+1$, $SVm+2$...] are delivered to a computational block 100 which calculates an average stroke volume value, denoted $SV_M$, by adding together the values of M measurements and then dividing by M. This process may be expressed:

$$SVM = 1/M \sum_{m=1}^{M} SVm$$

Experiments have been performed on dogs where the value of M has been varied from 1 to 12. The control algorithm appears to be relatively insensitive to this interval and a alue of $M=1$ may be taken as a representative value.

The measured value of average stroke volume $SV_M$ is compared with a reference value for stroke volume denoted $SV_R$. The value for $SV_R$ is calculated by functional block 112 which will be described shortly.

The comparison between $SV_M$ and the stroke volume set point $SV_R$ is accomplished by functional node 104 which calculates the difference between the two values yielding a difference value denoted $\Delta SV_M$.

The value of $\Delta SV_M$ is used to calculate a value of the change in heart rate value denoted $\Delta HR_n$ in the figure. This computation is performed in functional block 106. Experimental work has been performed with a linear relationship between $\Delta SV_M$ and the computed value of $\Delta HR_n$ expressed:

$$\Delta HR_n = K_3 SV_M$$

However other relationships satisfying the general expression $\Delta HR_n = f(\Delta SV_M)$ may prove workable.

The proportionality constant $K_3$ has units of, beats per minute/liter. The value of $K_3$ affects the response time of the system to changes in the measured stroke volume. It appears from animal experimentation that the value of $K_3$ is not critical for the stability of the system. A typical value for $K_3$ may be taken as 600 bpm/L.

The value of $\Delta HR_n$ computed as a function of $\Delta SV_M$ is used to update the existing value for heart rate denoted $HR_{n-1}$. This calculation is performed at node 108 where the value of change in heart rate ($\Delta HR_n$) is added to the preceding value of heart rate ($HR_{n-1}$). It is important that this operation preserves the sign of the change of heart rate, so that the updated value of heart rate can increase or decrease in comparison with the preceding value.

The updated value for heart rate ($HR_n$) is permitted to range between a minimum heart rate value (HRmin) and a maximum heart rate value (HRmax). The rate limit check is performed by functional block 110. The value of the heart rate delivered to the pulse generator 24 is denoted $HR_N$ where $HR_N = f(HR_n)$. The computed value for $HR_N$ replaces the prexisting value for $HR_{n-1}$ stored at 111, for use at node 108. This value is used to calculate a new value for the stroke volume reference value $SV_R$ at functional block 112 as follows.

The stroke volume reference value $SV_R$ is set to an initial value $SV_0$ during system initialization, (normal resting value). Subseqeunt values are computed as a function of the heart rate value, $SV_R = SV_0 + K_2 HR_{n-1}$ where the reference value is a linear function of the existing value of heart rate. However, other relationships satisfying the general expression: $SV_R = f(HR_{N-1})$ may prove workable.

Figure 3:
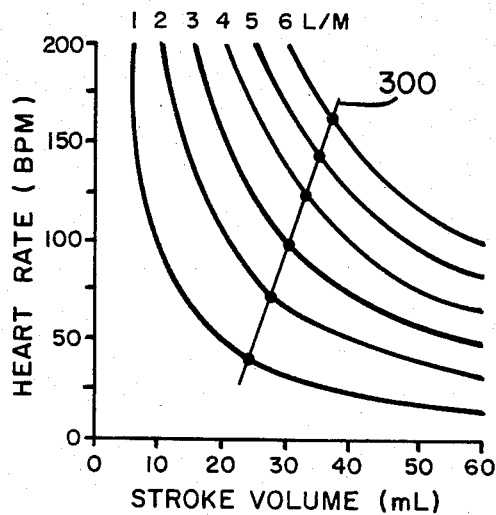
FIG. 3 is sequence of graphs which illustrate the relationship between the stroke volume and rate of the heart.
Figure 3:
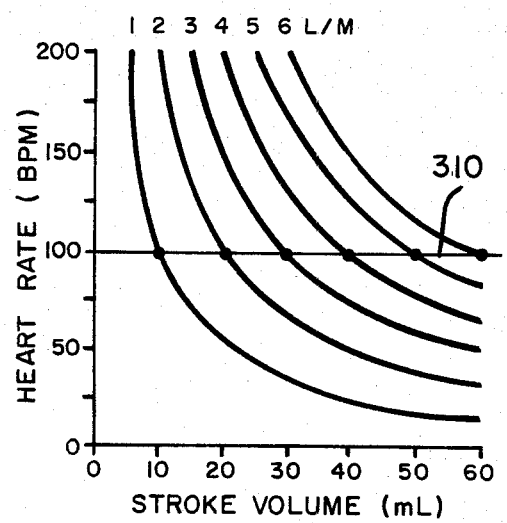
Figure 3:
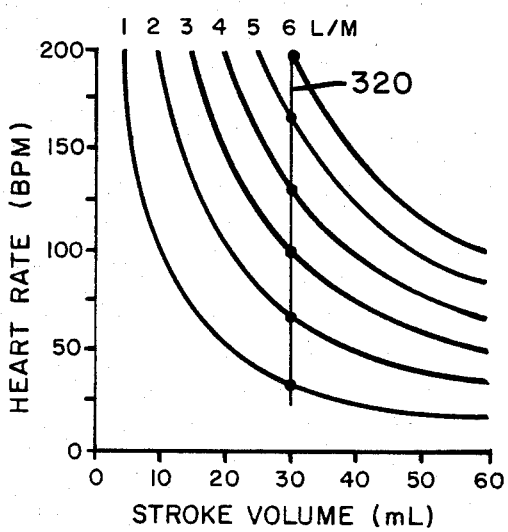
Figure 3:
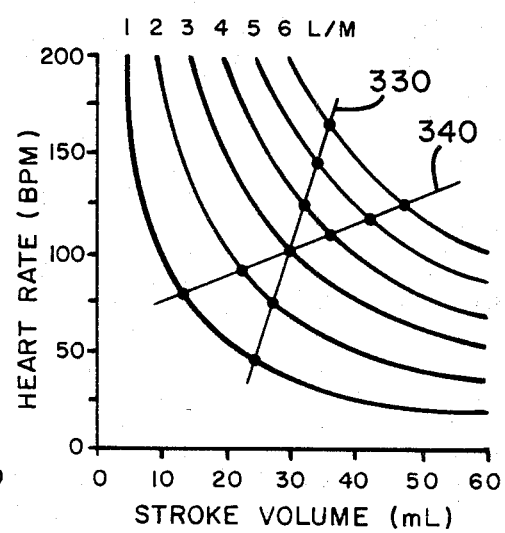

The value of $SV_0$ sets the operating point of the control system as will be discussed with reference to FIGS. 3c and 3d. The value of the proportionality constant $K_2$ controls the slope of the cardiac load line discussed in connection with FIGS. 3c and 3d.

The values for the averaging interval M, the initial stroke volume set point $SV_0$ and $K_2$ and $K_3$ are likely to be patient specific parameters and it may prove desirable to permit alteration of these values by the physician to adapt the pacer to the patient. Likewise, the values of HRmax and HRmin may be physician alterable to adapt the stimulation rate to the needs of the patient.

Pulse Generator System 24

The $HR_N$ signal is accepted by the pulse generator system 24 and interpreted as an escape interval for the pacemaker function of the device. In operation, the pacemaker escape interval will vary with the measured stroke volume of the heart. As previously indicated, during exercise the escape interval of the pacemaker will shorten. If the heart fails to beat within the designated escape interval, then a pacing stimulus will be provided, from pulse amplifier 27, to the heart through sensing stimulating electrode 11 as shown in FIG. 1. If a natural heart beat is detected prior to the expiration of the escape interval through sensing stimulating electrode 11, a sense amplifier 26 will inhibit the delivery of the pacing stimulus. Either or both chambers of the heart may be stimulated by the pulse generator and the device may operate in an inhibited mode. It should be recognized, however, that the stroke volume controlled system can be incorporated into an atrial tracking pacemaker modality wherein the ultimate escape interval of the pacemaker may be influenced by the detected atrial rate of the heart as well as by variations in the patient's cardiac stroke volume.

Operation

The objective of this stroke volume controlled pacer is to achieve a pacemaker escape interval which reflects the patient's physiologic demand for cardiac output.

The input signal to this control system is the stroke volume of the patient's heart and the output variable of this system is the pacemaker's escape interval.

Experimental data has been taken with a blood flow meter attached to the aorta of the heart, thus providing a direct measure of the stroke volume of the heart, on a beat by beat basis. It is expected, however, that for a fully implantable system it will be preferable to use the impedance plethysomography approach previously described. The integral of the mass flow rate signal from the transducer provides a sequence of stroke volume measurements SVm. These values may be averaged over a multiple number of cardiac cycles to provide a measure of the average stroke volume of the heart. If a very small number of cycles is used, it is possible that the beat-to-beat variation in the patient's stroke volume may cause the control system to generate a sequence of escape intervals which dither about a physiologically optimum escape rate. On the other hand, if the number of beats taken to form the average is large, the response time of the control system may be insufficient to provide the requisite cardiac output for the instantaneous work level of the patient. Experimental work indicates that a value of M=1 is suitable for a canine with induced heart block.

The average stroke volume value $SV_M$ is compared with a stroke volume reference value which may be selected by the physician and which is constrained within limits. If this stroke volume reference value is fixed at a specific stroke volume value, then the cardiac load line 320 as shown in FIG. 3c, will have an infinite slope. Under this regime, small increments in stroke volume due to increments in the exercise level of the object result in relatively large increments in heart rate, thus forcing the stroke volume of the heart back toward the set point reference $SV_R$. In this operating mode the patient is paced at a rate which results in a fixed stroke volume for the heart. Experimental research with canine reveals a potential defect of fixed stroke volume pacing. As indicated in FIG. 3c, an escape interval dictated by fixed stroke volume may call for heart rates substantially above those which are safe for the subject.

By permitting the stroke volume reference point value to vary within constrained limits, one can control the slope of the cardiac load line. Permitting the stroke volume reference point value to vary over a range of approximately 30 ml results in a control system response depicted by FIG. 3d.

In this system the instantaneous value of the stroke volume reference point $SV_R$ is a function of the instantaneous value of the heart rate. The linear relationship depicted by functional block 112 of FIG. 2 results in a cardiac load line 330 as shown in FIG. 3d. While a larger value of the portionality constant K2 as shown by curve 112b in FIG. 2 results in a cardiac load line similar to cardiac load line 340 in FIG. 3d. Thus, the proportionality constant K2 controls the slope of the cardiac load line and may vary the cardiac response from that observed in fixed rate pacing as depicted in FIG. 3b to that which results from pacing to a fixed stroke volume depicted in FIG. 3c. An appropriate value for K2 must be selected by the physician based upon information concerning the subject patient's heart contractility and stroke volume variations.

The initial value of the stroke volume set point is taken as $SV_0$ which may also be a physician programmable variable in the pacemaking system. This value controls the initial operating point for the system at resting values of cardiac output. The variation in stroke volume measurement computed at node 104 is utilized to calculate the change in heart rate of the pacemaker in node 106. Once again a linear relationship between the change in heart rate and the change in stroke volume is illustrated in FIG. 106. It is quite likely that other functions may be suitable for these relationships. The value of the proportionality constant K3 which controls the slope of the function controls the response time of the pacing system to changes in stroke volume of the patient.

Since it is desirable to have a fast acting system and it is desirable to have a large value of K3. In canine work values for the proportionality constant have varied from 156 bpm/L to 1250 bpm/L with a value of 600 bpm/L proving suitable for canines with induced heart block.

The calculated value of the change in the desired heart rate computed in functional block 106 is added to the existing value of the heart rate and if this new value falls within the limits prescribed by functional block 110 it is delivered to the pulse generator to control the pacing of the patient's heart. It is desirable to have the maximum and minimum heart rates for the system physician prescribed.

What is claimed is:

1. A cardiac pacer for the therapeutic stimulation of a heart comprising:
    lead system means for coupling said pacer to the patient's heart;
    measuring means coupled to said lead for inferring the stroke volume of said heart from the measurement of a physiologic parameter and for producing a measurement indicative of stroke volume;
    computation and control means coupled to said measuring means for determining a heart rate value in response to said stroke volume measurements wherein said heart rate is defined as the V—V interval;
    means for comparing the value of said stroke volume measurement with the value of a stroke volume set point for producing a stroke volume difference value;
    means for determining a heart rate difference value, wherein said heart rate value is defined as the V—V interval, from said stroke volume difference value;
    means for adding said heart rate difference value to the previous heart rate value yielding a current, heart rate value; and
    pulse generator means coupled to said lead system and said computational and control means for providing stimulation pulses to said heart at a frequency which is a function of said heart rate value.

2. A cardiac pacer for the therapeutic stimulation of a heart comprising:
    measuring means for periodically inferring the stroke volume of said heart and for roducing a sequence of stroke volume measurements;
    pulse generator means for providing stimulation pulses to said heart at a frequency proportional to a heart rate value wherein said heart rate value is defined as the V—V interval;
    means coupled to said measuring means and coupled to said pulse generator means for determining said heart rate value in response to stroke volume measurement;
    means for comparing the value of said stroke volume measurement with the value of a stroke volume set point for producing a stroke volume difference value;
    means for determining a heart rate difference value, wherein said heart rate value is defined as the V—V interval, from said stroke volume difference value; and
    means for adding said heart rate difference value to the previous heart rate value yielding a current, heart rate value.

3. A cardiac pacer for the therapeutic stimulation of a heart comprising:
    measuring means for measuring the ventricular volume of said heart at end diastole and at end systole and for inferring a stroke volume measurement from said end systolic and end diastolic measurements;
    pulse generator means for providing stimulation pulses to said heart at a frequency proportional to a heart rate value wherein said heart rate value is defined as the V—V interval;
    computational control means coupled to said measuring means and coupled to said pulse generator means for determining said heart rate value in response to the stroke volume measurement;

means for comparing the value of said stroke volume measurement with the value of a stroke volume set point for producing a stroke volume difference value;

means for determining a heart rate difference value, wherein said heart rate value is defined as the V—V interval, from said stroke volume difference value; and means for adding said heart rate difference value to the previous heart rate value yielding a current, heart rate value.

4. The cardiac pacer of claim 1 or claim 2 or claim 3 wherein said computation and control means further includes:

means for determining said stroke volume set point value from said heart rate value.

5. A method of controlling the escape rate of a pacer comprising the steps of:
 (a) measuring the cardiac stroke volume;
 (b) comparing the measured stroke volume with a stroke volume set point value yielding a stroke volume variation value;
 (c) calculating a heart rate variation value from said stroke volume variation value;
 (d) adding said heart rate variation value to an existing value of heart rate yielding a heart rate summation value;
 (e) calculating an updated heart rate value from said heart rate summation value; and
 (f) setting said escape rate in response to said updated heart rate value.

6. A method of controlling the escape rate of a pacer comprising the steps of:
 (a) measuring the cardiac stroke volume;
 (b) comparing the measured stroke volume with a stroke volume set point value yielding a stroke volume variation value;
 (c) calculating a heart rate variation value from said stroke volume variation value;
 (d) adding said heart rate variation value to an existing value of heart rate yielding a heart rate, summation value;
 (e) calculating an updated heart rate value from said heart rate summation value;
 (f) setting said escape rate in response to said updated heart rate value; and
 (g) calculating a stroke volume set point value from said heart rate value.

* * * * *

Disclaimer 4,535,774—*Walter H. Olson*, North Oaks, Minn., STROKE VOLUME CONTROLLED PACER. Patent dated Aug. 20, 1985. Disclaimer filed Jan. 17, 1992, by the assignee, Medtronic, Inc.

Hereby enters this disclaimer to claims 1-5 of said patent.

[*Official Gazette February 18, 1992*]